US006420177B1

(12) United States Patent
Weber et al.

(10) Patent No.: US 6,420,177 B1
(45) Date of Patent: *Jul. 16, 2002

(54) METHOD FOR STRAIN IMPROVEMENT OF THE ERYTHROMYCIN-PRODUCING BACTERIUM

(75) Inventors: J. Mark Weber; Minh B. Luu, both of Chicago, IL (US)

(73) Assignee: FermaLogic Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/153,599

(22) Filed: Sep. 15, 1998

Related U.S. Application Data

(60) Provisional application No. 60/059,079, filed on Sep. 16, 1997.

(51) Int. Cl.[7] .......................... C12N 15/74; C07H 21/04
(52) U.S. Cl. ...................... 435/477; 536/23.1; 536/23.2
(58) Field of Search .................. 435/477; 536/23.1, 536/23.2

(56) References Cited

PUBLICATIONS

Claudio D. Denoya et al., A *Streptomyces avermitilis* Gene Encoding a 4–Hydroxyphenylpyruvic Acid Dioxygenase–Like Protein That Directs the Production of Homogentisic Acid and an Ochronotic Pigment in *Escherichia coli*, Journal of Bacteriology, Sep. 1994, pp. 5312–5319, vol. 176, No. 17.

W. Claiborne Fuqua et al., Characterization of *mel*A: a gene encoding melanin biosynthesis from the marine bacterium *Shewanella colwelliana*, Gene, 1991, pp. 131–136, vol. 109.

Elizabeth E. Wyckoff et al., Coling and expression of a gene encoding a T–cell reactive protein from *Coccidiodes immitis*: homology to 4–hydroxyphenylpyruvate dioxygenase and the mammalian F antigen, Gene, 1995, pp. 107–111, vol. 161.

Ulla Rüetschi et al., Characterization of 4–hydroxyphenylpyruvate dioxygenase, Eur. J. Biochem., 1992, pp. 459–466, vol. 205.

J. Mark Weber et al., Organization of a Cluster of Erythromycin Genes in *Saccharopolyspora erythraea*, Journal of Bacteriology, May 1990, pp. 2372–2383, vol. 172, No. 5.

J. Mark Weber et al., The use of a chromosome integration vector to map erythromycin resistance and production genes in *Saccharopolyspora erythraea*(*Streptomyces erythraeus*), Gene, 1988, pp. 173–180, vol. 68.

*Primary Examiner*—Ponnathapu Achutamurthy
*Assistant Examiner*—Peter P. Tung
(74) *Attorney, Agent, or Firm*—Rockey, Milnamow & Katz, Ltd

(57) ABSTRACT

The present invention relates to a method of improving the strain used for the production of erythromycin through the disruption of the melA gene.

1 Claim, 6 Drawing Sheets

METHOD FOR STRAIN IMPROVEMENT OF THE ERYTHROMYCIN-PRODUCING BACTERIUM

RELATED APPLICATIONS

This application claims priority from U.S. Application No. 60/059,079 filed on Sep. 16, 1997.

GOVERNMENT FUNDING

Funds used to support some of the studies disclosed herein were provided by the United States Government (NIH Grant No. R44-AI34698-03.). The United States Government, therefore, may have certain rights in the invention.

TECHNICAL FIELD OF THE INVENTION

The field of this invention is erythromycin production. More particularly, the present invention pertains to a method of improving the strain used for the production of erythromycin through the disruption of the melA gene.

BACKGROUND OF THE INVENTION

Actinomycete fermentations are the source of many medically important pharmaceuticals, particularly antibiotics. The commercial production of these compounds is made more economical through genetic alterations in the producing organism, referred to as strain improvements, that are traditionally introduced through a random mutation and screening process (Queener, S. W. and D. H. Lively 1986. Screening and selection for strain improvement, p. 155–169. In Manual of Industrial Microbiology and Biotechnology. Eds. A. L. Demain and N. A. Solomon. American Society for Microbiology, Washington. 1986). The traditional process is tedious and time consuming, but is technically simple to perform. Its major drawback is that it is empirical; and during the 50 years that it has been practiced by industry, very little has been learned concerning the genetics of strain improvement.

More recently molecular genetic technology has been developed that allows for the introduction of "targeted" genetic alterations of industrially important strains. In particular, the erythromycin producing strain, *Sac. erythraea*, has a well developed system for integrative transformation, targeted gene replacement and disruption (Weber, J. M. and R. Losick, 1988, *Gene* 68, 173–180; Weber, J. M., J. O. Leung, G. T. Maine, R H. B. Potenz, T. J. Paulus and J. P. DeWitt, 1990, *J. Bacteriol.* 172, 2372–2383). This approach, though technically more difficult to perform, provides yield improvement results plus insight into the metabolic and genetic events that lead to strain improvement.

Although molecular genetic technology has been used in *Sac. erythraea* for the development of novel macrolide structures (Cortes, J., K. E. Wiesmann, G. A. Roberts, M. J. Brown, J. Staunton, and P. F. Leadlay, 1995, *Science* 268:1487–1489.; Donadio, S., J. B. McAlpine, P. A. Sheldon, M. A. Jackson, L. Katz, 1993, *PNAS* USA 90:7119–7123), it has not yet been applied to the area of erythromycin strain improvement.

Current strain improvement technology consists of an empirical and labor intensive process of introducing randomly produced mutations followed by large-scale brute-force screening for better strains. Targeted gene disruption is a way to rationally modify a strain of Saccharopolyspora to overproduce erythromycin. Currently there are no other genes described whose inactivation will lead specifically and reproducibly to an improved erythromycin-producing strain. Erythromycin is a bulk pharmaceutical produced in the thousands of metric tons per year and the market for this bulk compound is approximately 600 million dollars per year. Any improvement in the production process that would lead to substantial increases in production would have significant economic implications.

BRIEF SUMMARY OF THE INVENTION

The method of the invention, herein described, includes the genetic modification of an erythromycin-producing microorganism through the targeted disruption of the melA gene with plasmid pFL1046 so that the microorganism is transformed into a more efficient and more robust producer of erythromycin under conditions where oxygen is a limiting nutrient. Plasmid pFL1046 is a derivative of plasmid pFL14 which was isolated from a library of *Sac. erythraea* DNA fragments found during a visual blue-pigment screening procedure in *S. lividans*. The DNA sequence of a subclone of pFL14, pFL1040, is shown in FIG. 1 (SEQ ID NO:1) showing the coding sequence of the melA gene (SEQ ID NO:2) from *Sac. erythraea*. The alignment of the deduced amino acid sequence of the melA gene (SEQ ID NO:3) from *Sac. erythraea* is compared to the sequence of melA genes from other organisms (FIG. 3 SEQ ID NOS:6–11). A very high degree of homology is seen to these other melA genes which further supports the fact that this gene is in fact involved in pigment biosynthesis in *Sac. erythraea*.

According to one aspect of the method of the invention, transformation of an erythromycin-producing microorganism into a more robust producer is accomplished by integrating, via homologous recombination, a plasmid constructed from a parent vector, pFL8 and a DNA fragment from the *Sac. erythraea* chromosome which is internal to the coding sequence of the 4-hydroxyphenylpyrivic acid dioxygenase (melA) gene. Integrative transformation of this plasmid into the *Sac. erythraea* chromosome disrupts the normal function of the melA gene which consequently blocks the production of pyomelanin pigment and slows the growth of the organism. This integrative plasmid is constructed to be capable of being stably maintained in the microorganism (i.e., of being passed faithfully in its active form from one generation to the next).

A microorganism embodying the present invention is a novel strain of *Sac. erythraea* with lower oxygen requirements for the production of erythromycin in an aqueous medium containing assimilable sources of nitrogen and carbon. The blockage of metabolic flow of oxygen into pigment biosynthesis and tyrosine metabolism reduces the strains requirement for oxygen, and indirectly slows the growth of the strain, but does not negatively affect erythromycin biosynthesis.

BRIEF DESCRIPTION OF THE DRAWINGS

FIG. 1 shows the nucleotide sequence and deduced amino acid sequence of the melA gene from *Sac. erythraea* and two incomplete open reading frames flanking melA on clone PFL1040. The nucleotide sequence between the convergent dashed arrows indicates the region that was amplified by PCR and cloned to make integrative plasmid pFL1046 which was used for the targeted disruption of the melA gene in the chromosome of *Sac. erythraea*. The putative ribosome binding site (GGGAGG) for the melA gene is also shown (underlined) and is located 6 bp upstream of the putative GTG start codon. Also shown are two ApaI sites internal to the melA coding sequence that mark the boundaries of the DNA fragment that was used to prepare the probe for Southern hybridizations.

Figure 3:
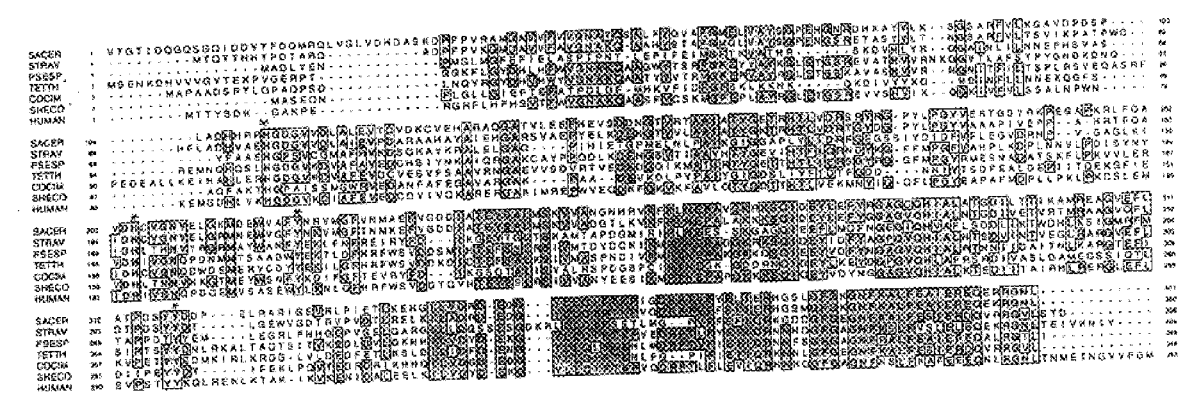

FIG. 3 shows the alignment of the deduced amino acid sequence of the HPD-like proteins. Comparison of sequences from *Sac. erythraea* (SACER) and *S. avermitilis* (STRAV) ((Denoya et al., 1994, *J. Bacteriology* 176 (17): 5312–5319) and five additional sequences from other organisms. PSESP, *Pseudomonas* species (Ruetschi, U., B. Odelhog, S. Lindstedt, J. Barros-Soderling, B. Persson, and H. Jorvall, 1992, *Eur. J. Biochem.* 205:459–466); TETTH, *T. thermophila* F antigen (Hummel, R., P. Norgaard, P. H. Andreasen, S. Neve, K. Skjodt, D. Tornehave, and K. Kristiansen, 1992, *J. Mol. Biol.* 228:850–861); COIIM, *Coccidioides immitis* (Wyckoff, E. E., E. J. Pishko, T. N. Kirkland, and G. T. Cole, 1995, *Gene* 161:107–111); SHECO, *Shewanella colwelliana* (Fuqua, W. C., V. E. Coyne, D. C. Stein, C.-M. Lin, and R. M. Weiner, 1991, *Gene* 109:131–136); HUMAN, (Ruetschi, U., A. Dellsen, P. Sahlin, G. Stenman, L. Rymo, and S. Lindstedt, 1993, *Eur. J. Biochem.* 213:1081–1089). Shaded boxes indicate regions of identity. Dashes indicate gaps introduced to maximize alignment.

DETAILED DESCRIPTION OF THE INVENTION

Figure 2:
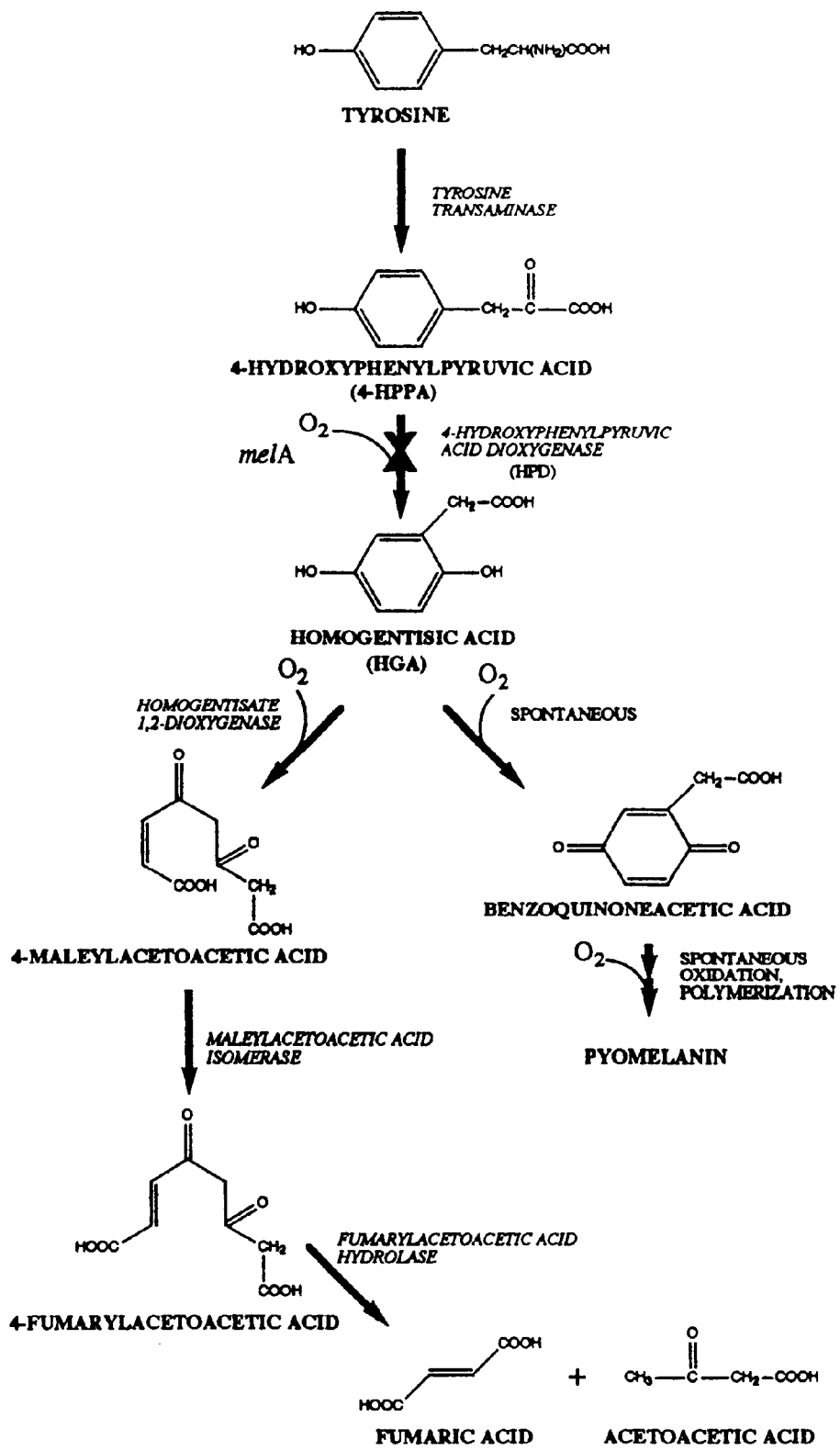
FIG. 2 shows the proposed metabolic pathway for the catabolism of tyrosine in *Sac. erythraea* showing the biochemical step in which the HPD enzyme acts in the biosynthesis of pyomelanin pigments. The arrow marked with an "X" represents the step in the pigment biosynthetic pathway that is blocked by the targeted disruption of the melA gene as described in the text. The disruption in the function of melA results in the block in tyrosine catabolism and pigment production.

Bacterial strains and plasmids. The FL359 strain of *Saccharopolyspora erythraea* ATCC 11635 was used as the parent strain and the host in transformation experiments. This strain was obtained from the ATCC11635 strain. The DH5alpha strain (Hanahan, 1983) was used for experiments performed in *E. coli*.

Chemicals and Biochemical Reagents. Erythromycin A (Em), tetrazolium chloride, was obtained from Sigma. Thiostrepton (Ts) was provided by S. J. Lucania (Bristol Meyers Squibb, N.J.).

Media and handling. E20A agar medium per 1 liter aqueous solution: 5 g bacto-soytone, 5 g soluble starch, 3 g $CaCO_3$, 2.1 g MOPS buffer, and 20 g bacto-agar. E29F broth medium for 1 liter: 22 g nutrisoy flour (ADM); 15 g soluble starch (Difco); 3 g $CaCO_3$ (J. T. Baker); *0.5 g $MgSO_4$·$7H_2O$; *0.015 g $FeSO_4$·$7H_2O$, 50 ml soybean oil. R2T2 regeneration plates (Weber, J. M., B. Schoner, and R. Losick, 1989, *Gene* 75, 235–241; Weber, J. M., C. K. Wierman, and C. R. Hutchinson, 1985, *J. Bacteriol.* 164, 425–433) were used for the selection of transformants using both *Sac. erythraea* and *S. lividans* host strains. Tryptic Soy Broth (TSB, Difco Laboratories, Detroit, Mich.), prepared according to manufacturers recommendations.

Figure 1:
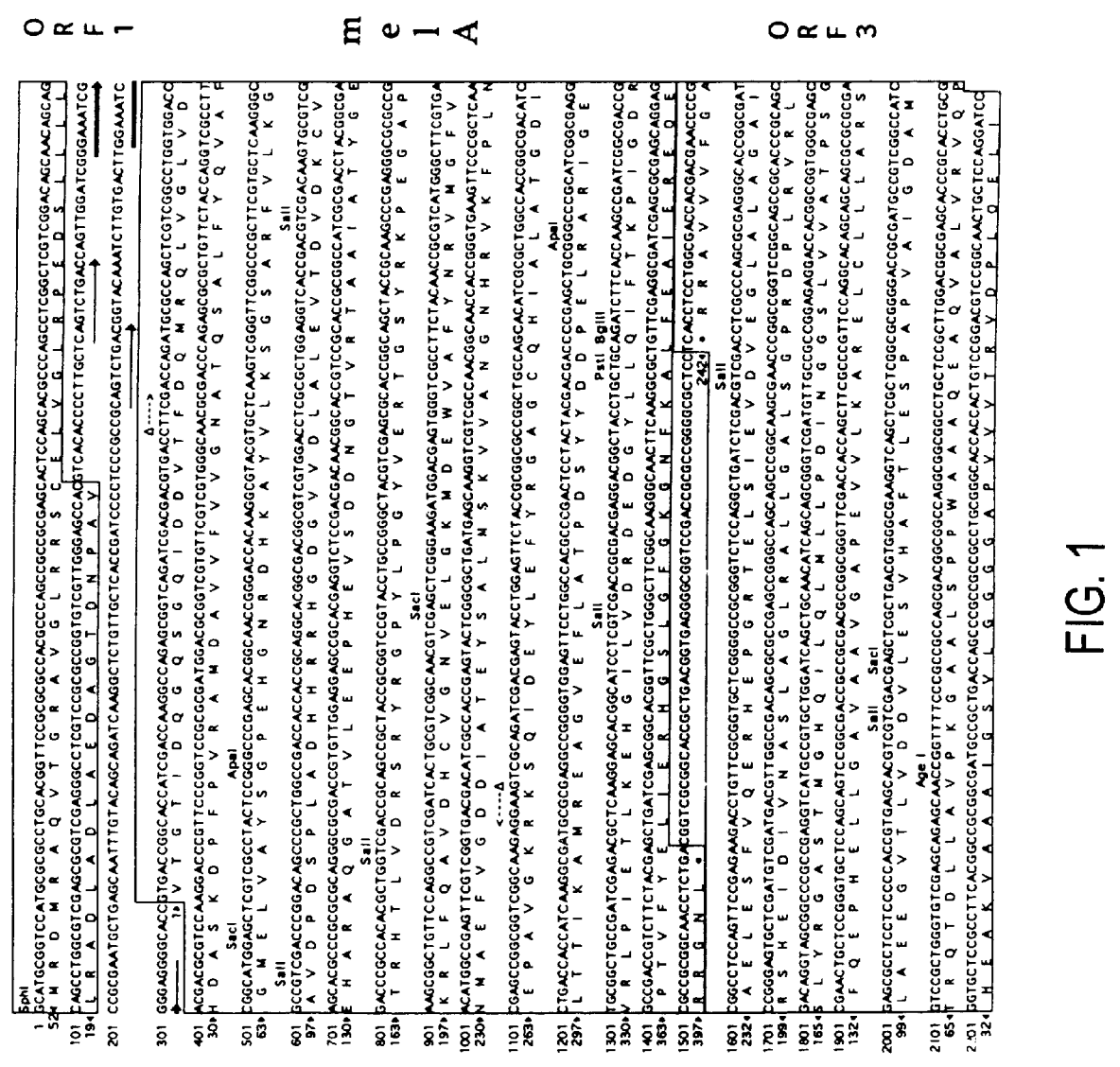

Construction of pFL1046. PCR primer sequences used for amplification of the melA gene-fragment cloned into pFL1046 were the following: 5"gtaagcttcgaccagatgcgccag3" (SEQ ID NO:12) and 5"tggaattccctcttgccgaccgcc3" (SEQ ID NO:13). The location of the primer sequences and the direction of primer elongation are indicated in the DNA sequence diagram (FIG. 1). EcoRI and HindIII restriction sites were added to the ends of the primers to facilitate cloning of the final PCR product into the multicloning region of plasmid pFL8.

Fermentation protocol for the production of erythromycin by *Sac. erythraea* under oxygen-limitation conditions in shake flasks. Spores of *Sac. erythraea* were transferred aseptically from a slant or plate culture to 4 mL of sterile TSB broth in duplicate 16×125 mm capped test tubes. Test tube cultures were grown in a shaker for 2 days at 32° C. at a 10° angle. The contents of one tube (3.5 mL due to evaporation) were mixed with the duplicate tube. A 3 mL portion of the mixture was transferred to 30 mL of E29F medium. Note that oxygen limitation conditions were determined empirically to be encountered in 250 ml shake flasks containing 30 ml of broth or more and shaking at 500 rpm on a shaker with a one inch circular orbit. Weights were recorded of flasks after inoculation; the cultures were grown in 250 mL non-baffled shake flasks for 5 days at 32° C., 500 rpm (one inch rotary displacement). After 5 days, the color of the culture was recorded and the flasks were re-weighed and adjusted to their original weight through the addition of water to compensate for water lost due to evaporation. The cultures were also streaked onto agar plates to check for contamination. Cells were then pelleted by centrifugation and the broth was decanted into 50 mL plastic Corning tubes for storage at 4° C. until they were bioassayed. Broth was diluted 1:4 with sterile water prior to bioassay.

Bioassay for erythromycin. A large plate (Corning Costar, Cambridge, Mass., 245 mm square bioassay dish cat. no. 431111), double-agar layer system was used. The bottom agar layer consisted of 100 mL TSB agar. Once solidified (sitting 1 hour at room temperature) a top agar layer was poured. Top agar consisted of 100 mL TSB agar containing 200 μL 1% tetrazolium red and a sufficient quantity of *B. subtilis* thiostrepton-resistant spores to produce a confluent lawn of growth. The upper layer was solidified at room temperature for 1 hour with lid slightly open, or the plate was placed open in a laminar flow hood to remove any moisture from the surface of the plate. Broth samples were spotted (15 μL) onto ¼ inch bioassay discs (Schleicher and Schuell, Keene, N.H.) and let dry for 30 min. Standard erythromycin solutions were prepared at 5, 10, 25, 50, 100, and 250 μg/mL and used to wet bioassay discs which were dried and stored at room temperature and placed onto the plate at the time the dried experimental samples were applied. The bioassay plate was incubated overnight at 37° C. Following incubation, the zones were measured, and converted to concentrations using the standard curve produced for each plate.

Cloning and analysis of the melA gene from *Sac. erythraea*. As part of a study to identify genes that affect erythromycin biosynthesis, a genomic library of *Sac. erythraea* DNA was screened for clones that stimulated the production of blue pigments in *S. lividans*. One of these clones, pFL14, carried in the Streptomyces/*E. coli* bifunctional plasmid pFL8 was found to stimulate blue pigment production in the presence of thiostrepton and soybean media.

Figure 4B:
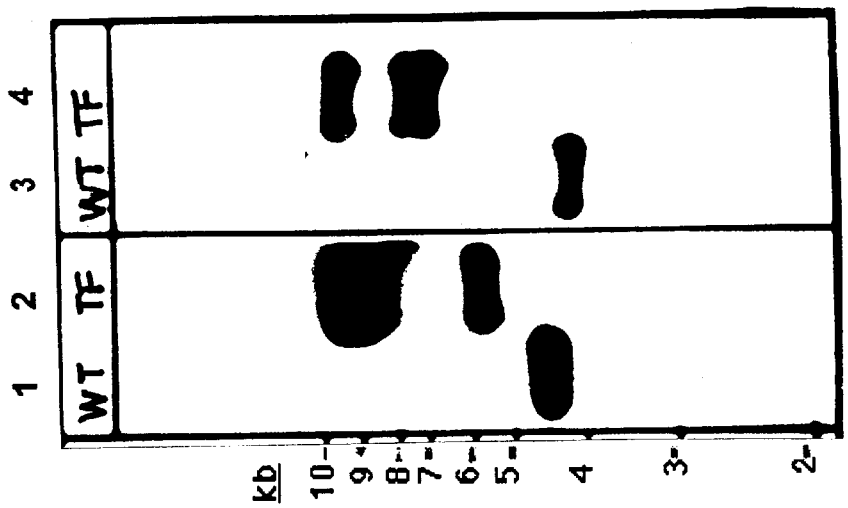
FIG. 4 shows an analysis of DNA from the melA-targeted disruption experiment. A. Diagram of insertion of plasmid pFL1046 (circle, top) into the chromosome of *Sac. erythraea*. Rectangle overlaying the melA arrow on the chromosome represents the area of cloned DNA which directed integration of the plasmid by homologous recombination into the chromosome. B. Southern analysis of chromosomal DNA from the parental and pFL1046 transformant strain. Purified DNA from the *Sac. erythraea* parent strain and the pFL1046 transformant strain was digested with BamHI or PstI, and DNA fragments were separated on a 0.8% agarose gel and transferred to nylon sheets (Hybond-N+, Amersham, UK) by a modification of the method of Southern (1975). Nylon sheets were probed with a DNA fragment that had been labeled using the Genius 1 (DIG) DNA labeling and detection kit (Cat. No. 1093 657). The DNA fragment used as the probe was prepared from plasmid pFL1040 digested with ApaI to prepare a 762 bp fragment that was purified using GeneClean (Bio101, La Jolla, Calif.). The nucleotide sequence of the DNA fragment used as the probe is shown between the two ApaI sites (FIG. 1). C. Southern analysis showing a single hybridizing band for all Actinomycete strains tested except for *S. azureus*.
Figure 4A:
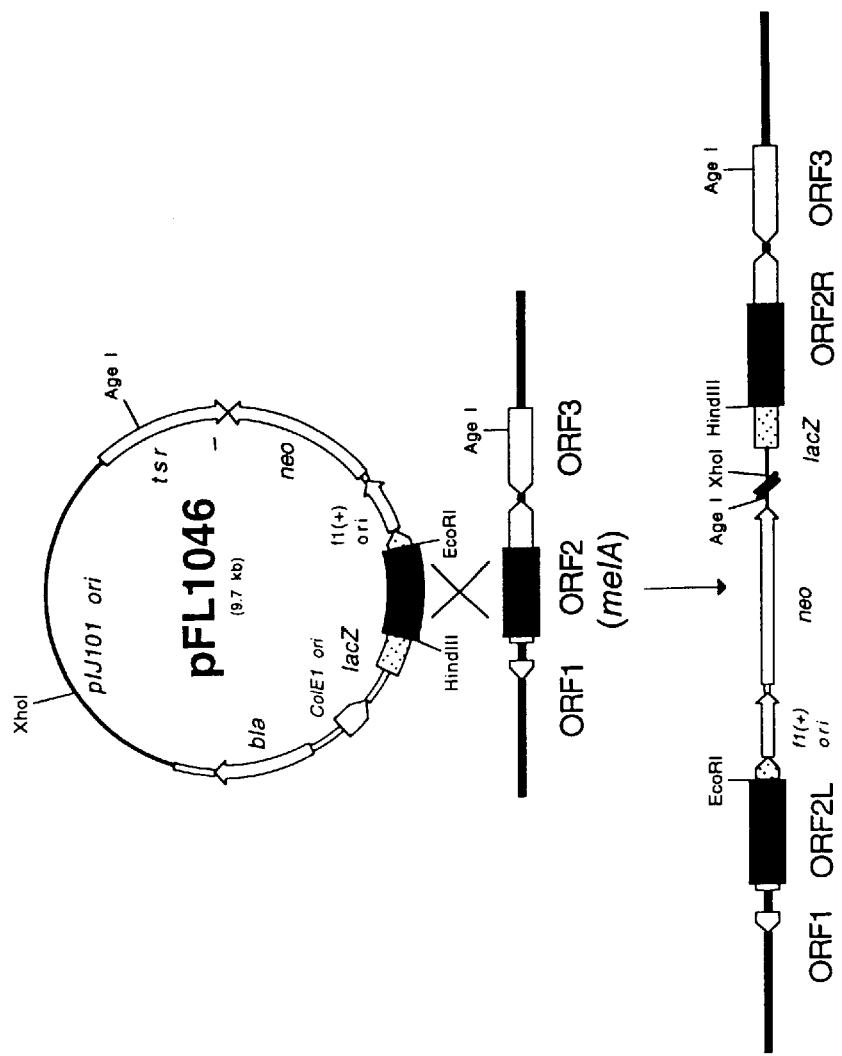

Following the identification of plasmid pFL14 from the *S. lividans* prescreen, it was subsequently introduced in high copy into *E. coli* DH5alpha and found to cause production of brown pigments in liquid culture. Production of brown pigment was enhanced through subcloning to form the plasmid pFL1040 and supplementation of the growth medium with the amino acid L-tyrosine. Subsequently, subcloning and DNA sequence analysis (FIG. 1) revealed several open reading frames on this clone, but only one complete ORF was found on the clone and it was found to be responsible for the formation of the brown pigment in *E. coli*. This ORF was found to be homologous to a melA-like gene previously reported from *S. avermitilis*, involved in brown pigment biosynthesis in that strain and capable of producing brown pigment in *E. coli* as well ((Denoya et al., 1994, *J. Bacteriology* 176 (17): 5312–5319). The workers in *S. avermitilis* found that the deduced amino acid sequence of the gene showed a high degree of identity to the enzyme 4-hydroxyphenylpyruvic acid dioxygenase involved in the pyomelanin pigment biosynthetic pathway (FIG. 2); the alignment of the predicted amino acid sequences of the two melA genes from *Sac. erythraea* and *S. avermitilis* showed that they were 63.5% identical over the complete sequence (FIG. 4A). The melA genes of *Streptomyces avermitilis* and *Sac. erythraea* also show striking homology to genes from more distantly related species, including humans (Denoya et al., 1994, *J. Bacteriology* 176 (17): 5312–5319). While it is clear from our results and others that the melA gene is not essential for survival of Actinomycete species, the conservation of its amino acid sequence and the widespread occurrence of the gene in nature indicates it has played a critical role during evolution.

Targeted disruption of the melA gene and effect on brown pigment formation. In order to disrupt melA, a 761 bp DNA fragment was generated by PCR which was internal to the coding sequence of the gene (FIG. 1 SEQ ID NOS: 1 and 2). This internal fragment was cloned into plasmid pFL8 to generate pFL1046 (FIG. 4A) which was integratively transformed into *Sac. erythraea* ATCC 11635. Thiostrepton-resistant transformants of *Sac. erythraea* were obtained and analyzed by Southern analysis showing that the plasmid had inserted into the melA gene in the chromosome (FIG. 4B).

The disrupted strain was plated on E20A and E29F agar media with and without L-tyrosine supplementation. After one week incubation at 32° C. the colonies growing on E29F agar with tyrosine supplementation were dark brown in color, they also secreted a dark brown pigment in the surrounding medium. The E29F plates not containing tyrosine supplementation were also brown, but not as dark as the plates containing tyrosine. On E20A plates, which is the standard agar medium for this strain, brown pigment production was not observed even on the agar containing additional tyrosine.

Figure 4C:
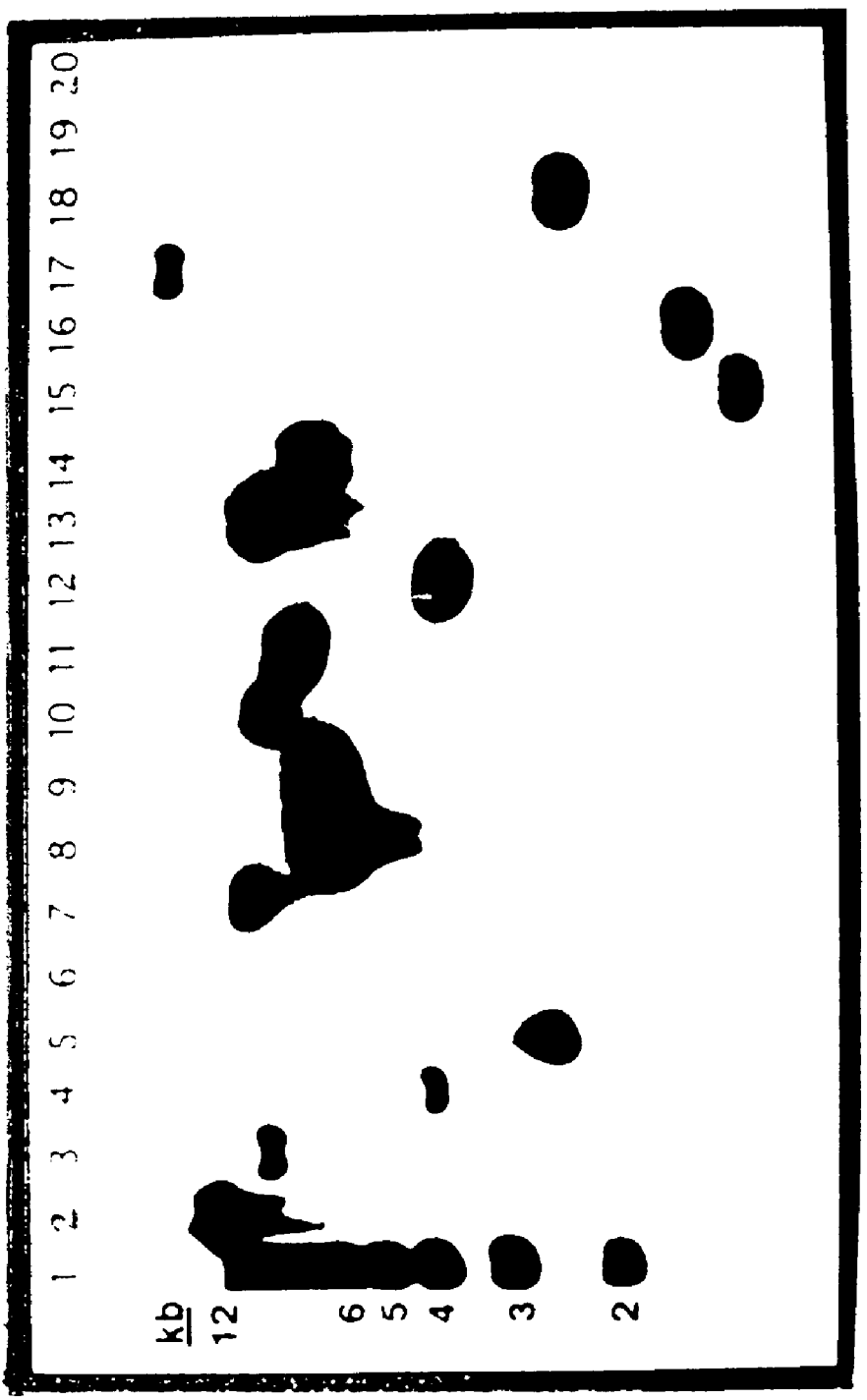

Survey of commercial and academic Actinomycete strains for melA homologs. Strains used for the commercial production of other antibiotics were obtained from the Ferma-Logic collection or the American Type Culture Collection (ATCC) and used for the preparation of total DNA from each strain. Total DNA was digested with BamHI and PstI and Southern blots were prepared for the two sets of digests with each enzyme and probed with a 762 bp internal ApaI fragment from the melA gene (FIG. 1 SEQ ID NOS: 1 and 2) from *Sac. erythraea*. The results (FIG. 4C) show clearly a single hybridizing band for all the Actinomycete strains tested except for one, *S. azureus*, the producer of thiostrepton, which showed no hybridizing band in either the BamHI digest or the PstI digest. The conditions used in the hybridization were stringent (65° C.), and yet the hybridizing bands produced a clear strong signal with little background indicating a high degree of homology between the probe DNA from *Sac. erythraea* and the homologous genes from the various species. The two non Actinomycete strains, *E. coli*, and *B. subtilis*, failed to show even a faint signal in this assay.

Figure 5:
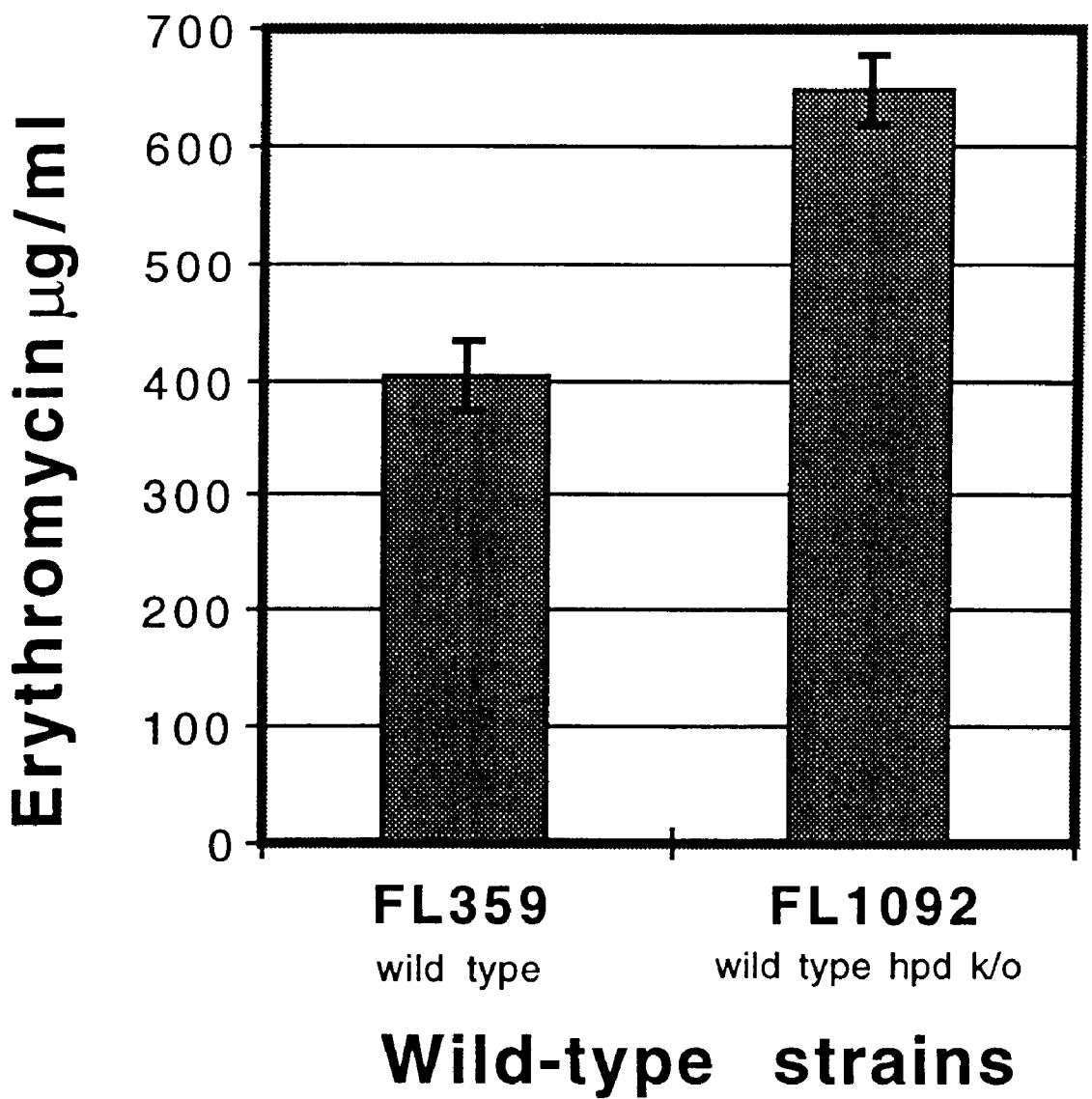
FIG. 5 shows the effect of melA disruption on the production of erythromycin by *Sac. erythraea*. Fermentations were performed according to the method described hereinafter. Erythromycin concentrations were determined by the agar plate bioassay method, also described hereinafter.

Effect of disruption of melA on erythromycin production. A comparative analysis of the parent strain and the melA blocked strain was performed in shake flask fermentations, as described above, to determine the effect of the melA mutation on the production of erythromycin. The results indicated that the melA blocked strain is a more robust strain and repeatedly produced significantly higher concentrations of erythromycin than the parent strain under conditions of oxygen limitation (FIG. 5). This is important because many Actinomycete fermentations are limited by oxygen supply, and the economic loss of low yielding fermenter runs due to oxygen stress can be significant. The amount of the increase was consistently in excess of 50% over several experiments performed on different occasions. Culture broth extracts were inspected by thin layer chromatography; the results show that the increase in bioactivity observed in the bioassay is due to an increase in production of erythromycin A, which is the most active and most desired product of the fermentation.

The present invention provides a simple method for improving the erythromycin production efficiency of the *Sac. erythraea* fermentation under conditions of oxygen limitation. The yield improvement effect is caused by the targeted disruption of an melA-like gene, which is required for the biosynthesis of brown pigments. The mutation involves the targeted insertion of a plasmid, pFL1046 by homologous recombination into to the coding sequence of melA in such a way that transcription of melA is disrupted.

If the plasmid insertion mutation described here is found to be beneficial to a commercial strain, a permanent mutation not involving the maintenance of a plasmid in the chromosome could be created using gene replacement technology that is well established for this strain (Weber, J. M., J. O. Leung, G. T. Maine, R H. B. Potenz, T. J. Paulus and J. P. DeWitt, 1990, *J. Bacteriol.* 172, 2372–2383). This would create a permanent mutation that would not require maintenance of foreign DNA in the genome.

What is claimed is:

1. A method for modifying a strain of *Saccharopolyspora erythraea* containing a melA gene and which produces erythromycin, the method comprising the step of integrating into said strain of *Saccharopolyspora erythraea* a plasmid which prevents proper transcription of the melA gene, wherein said plasmid is plasmid pFL1046 deposited with the Agricultural Research Service Culture Collection having Accession No. B-30276.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
       (A) LENGTH: 2299 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

| | | | | | |
|---|---|---|---|---|---|
| GCATGCGGTC | CATGCGCGCC | TGCACGGTTC | CGCGCGCCAC | GCCCAGCCGC | CGCGAGCACT | 60 |
| CCAGCACGCC | CAGCCTCGGC | TCGTCGGACA | GCAACAGCAG | CAGCCTGGCG | TCGAGCGCGT | 120 |
| CGAGGGCCTC | GTCCGCGCCG | GTGTCGTTGG | GAGCCACGTC | ACACCCCTTG | CTCAGTCTGA | 180 |
| CCAGTTGGAT | CGGGAAATCG | CCGCGAATGC | TGAGCAATTT | GTACAGCAGA | TCAAGGCTCT | 240 |
| GTTGCTCACC | GATCCCCTCC | CGCCGCAGTC | TGACGGTACA | AATCTTGTGA | CTTGGAAATC | 300 |
| GGGAGGGGCA | CCGTGACCGG | CACCATCGAC | CAAGGCCAGA | GCGGTCAGAT | CGACGACGTG | 360 |
| ACCTTCGACC | AGATGCGCCA | GCTCGTCGGC | CTGGTGGACC | ACGACGCGTC | CAAGGACCCG | 420 |
| TTCCCGGTCC | GCGCGATGGA | CGCGGTCGTG | TTCGTCGTGG | GCAACGCGAC | CCAGAGCGCG | 480 |
| CTGTTCTACC | AGGTCGCCTT | CGGCATGGAG | CTCGTCGCCT | ACTCCGGGCC | CGAGCACGGC | 540 |
| AACCGGGACC | ACAAGGCGTA | CGTGCTCAAG | TCGGGTTCGG | CCCGCTTCGT | GCTCAAGGGC | 600 |
| GCCGTCGACC | CGGACAGCCC | GCTGGCCGAC | CACCACCGCA | GGCACGGCGA | CGGCGTCGTG | 660 |
| GACCTCGCGC | TGGAGGTCAC | CGACGTCGAC | AAGTGCGTCG | AGCACGCCCG | CGCGCAGGGC | 720 |
| GCGACCGTGT | TGGAGGAGCC | GCACGAGGTC | TCCGACGACA | ACGGCACCGT | CCGCACCGCG | 780 |
| GCCATCGCGA | CCTACGGCGA | GACCCGCCAC | ACGCTGGTCG | ACCGCAGCCG | CTACCGCGGT | 840 |
| CCGTACCTGC | CGGGCTACGT | CGAGCGCACC | GGCAGCTACC | GCAAGCCCGA | GGGCGCGCCG | 900 |
| AAGCGGCTGT | TCCAGGCCGT | CGATCACTGC | GTCGGCAACG | TCGAGCTCGG | GAAGATGGAC | 960 |
| GAGTGGGTCG | CCTTCTACAA | CCGCGTCATG | GGCTTCGTGA | ACATGGCCGA | GTTCGTCGGT | 1020 |
| GACGACATCG | CCACCGAGTA | CTCGGCGCTG | ATGAGCAAGG | TCGTCGCCAA | CGGCAACCAC | 1080 |
| CGGGTGAAGT | TCCCGCTCAA | CGAGCCGGCG | GTCGGCAAGA | GGAAGTCGCA | GATCGACGAG | 1140 |
| TACCTGGAGT | TCTACCGCGG | CGCCGGCTGC | CAGCACATCG | CGCTGGCCAC | CGGCGACATC | 1200 |
| CTGACCACCA | TCAAGGCGAT | GCGCGAGGCC | GGGGTGGAGT | TCCTGGCCAC | GCCCGACTCC | 1260 |
| TACTACGACG | ACCCCGAGCT | GCGGGCCCGC | ATCGGCGAGG | TGCGGCTGCC | GATCGAGACG | 1320 |
| CTCAAGGAGC | ACGGCATCCT | CGTCGACCGC | GACGAGGACG | GCTACCTGCT | GCAGATCTTC | 1380 |
| ACCAAGCCGA | TCGGCGACCG | GCCGACCGTC | TTCTACGAGC | TGATCGAGCG | GCACGGTTCG | 1440 |
| CTGGGCTTCG | GCAAGGGCAA | CTTCAAGGCG | CTGTTCGAGG | CGATCGAGCG | CGAGCAGGAG | 1500 |
| CGCCGCGGCA | ACCTCTGACG | GTCGCGGCAC | CGCTGACGGT | GAGGGCGGT | CCGACCGCGC | 1560 |
| CGGGGCGCTC | CTCACCTCCT | GGCGACCACG | ACGAACCCCG | CGGCCTCCAG | TTCCGAGAAG | 1620 |
| ACCTGTTCGC | GGTGCTCGGG | GCCGCGGGTC | TCCAGGCTGA | TCTCGACGTC | GACCTCGCCC | 1680 |
| AGCGCGAGGG | CACCGGCGAT | CCGGGAGTGC | TCGATGTCGA | TGACGTTGGC | CGACAGCGCG | 1740 |
| CCGAGCCGGG | CCAGCAGCCC | GGCAAGCGAA | CCCGGCCGGT | CCGGCAGCCG | CACCCGCAGC | 1800 |

```
GACAGGTAGC GGCCCGCCGA GGTCATGCCG TGCTGGATCA GCTGCAACAT CAGCAGCGGG      1860

TCGATGTTGC CGCCGGAGAG GACCACGGCG GTGGGCGAGC CGAACTGCTC CGGGTGCTCC      1920

AGCAGTCCGG CGACCGCCGC GACGCCGGCG GGTTCGACCA CCAGCTTCGC CCGTTCCAGG      1980

CACAGCAGCA GCGCGCGCGA GAGCGCCTCC TCCCCCACCG TGAGCACGTC GTCGACGAGC      2040

TCGCTGACGT GGGCGAAGGT CAGCTCGCTC GGCGCGGGGA CCGCGATGCC GTCGGCCATC      2100

GTCCGCTGGG TGTCGAGCAG AGCAACCGGT TTTCCCGCCG CCAGCGACGG CGGCCAGGCG      2160

GCGGCCTGCT CCGCTTGGAC GGCGAGCACC CGCACCTGCG GGTGCTCCGC CTTCACGGCC      2220

GCGGCGATGC CGCTGACCAG CCCGCCGCCG CCTGCGGGCA CCACCACTGT CCGGACGTCC      2280

GGCAACTGCT CCAGGATCC                                                   2299
```

(2) INFORMATION FOR SEQ ID NO:2:

(i) SEQUENCE CHARACTERISTICS:
        (A) LENGTH: 1206 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1203

(xi) SEQUENCE DESCRIPTION: SEQ ID NO:2:

```
GTG ACC GGC ACC ATC GAC CAA GGC CAG AGC GGT CAG ATC GAC GAC GTG         48
Val Thr Gly Thr Ile Asp Gln Gly Gln Ser Gly Gln Ile Asp Asp Val
 1               5                  10                  15

ACC TTC GAC CAG ATG CGC CAG CTC GTC GGC CTG GTG GAC CAC GAC GCG         96
Thr Phe Asp Gln Met Arg Gln Leu Val Gly Leu Val Asp His Asp Ala
                20                  25                  30

TCC AAG GAC CCG TTC CCG GTC CGC GCG ATG GAC GCG GTC GTG TTC GTC        144
Ser Lys Asp Pro Phe Pro Val Arg Ala Met Asp Ala Val Val Phe Val
            35                  40                  45

GTG GGC AAC GCG ACC CAG AGC GCG CTG TTC TAC CAG GTC GCC TTC GGC        192
Val Gly Asn Ala Thr Gln Ser Ala Leu Phe Tyr Gln Val Ala Phe Gly
 50                  55                  60

ATG GAG CTC GTC GCC TAC TCC GGG CCC GAG CAC GGC AAC CGG GAC CAC        240
Met Glu Leu Val Ala Tyr Ser Gly Pro Glu His Gly Asn Arg Asp His
 65                  70                  75                  80

AAG GCG TAC GTG CTC AAG TCG GGT TCG GCC CGC TTC GTG CTC AAG GGC        288
Lys Ala Tyr Val Leu Lys Ser Gly Ser Ala Arg Phe Val Leu Lys Gly
                85                  90                  95

GCC GTC GAC CCG GAC AGC CCG CTG GCC GAC CAC CAC CGC AGG CAC GGC        336
Ala Val Asp Pro Asp Ser Pro Leu Ala Asp His His Arg Arg His Gly
            100                 105                 110

GAC GGC GTC GTG GAC CTC GCG CTG GAG GTC ACC GAC GTC GAC AAG TGC        384
Asp Gly Val Val Asp Leu Ala Leu Glu Val Thr Asp Val Asp Lys Cys
        115                 120                 125

GTC GAG CAC GCC CGC GCG CAG GGC GCG ACC GTG TTG GAG GAG CCG CAC        432
Val Glu His Ala Arg Ala Gln Gly Ala Thr Val Leu Glu Glu Pro His
    130                 135                 140

GAG GTC TCC GAC GAC AAC GGC ACC GTC CGC ACC GCG GCC ATC GCG ACC        480
Glu Val Ser Asp Asp Asn Gly Thr Val Arg Thr Ala Ala Ile Ala Thr
145                 150                 155                 160

TAC GGC GAG ACC CGC CAC ACG CTG GTC GAC CGC AGC CGC TAC CGC GGT        528
Tyr Gly Glu Thr Arg His Thr Leu Val Asp Arg Ser Arg Tyr Arg Gly
                165                 170                 175
```

```
CCG TAC CTG CCG GGC TAC GTC GAG CGC ACC GGC AGC TAC CGC AAG CCC      576
Pro Tyr Leu Pro Gly Tyr Val Glu Arg Thr Gly Ser Tyr Arg Lys Pro
            180                 185                 190

GAG GGC GCG CCG AAG CGG CTG TTC CAG GCC GTC GAT CAC TGC GTC GGC      624
Glu Gly Ala Pro Lys Arg Leu Phe Gln Ala Val Asp His Cys Val Gly
        195                 200                 205

AAC GTC GAG CTC GGG AAG ATG GAC GAG TGG GTC GCC TTC TAC AAC CGC      672
Asn Val Glu Leu Gly Lys Met Asp Glu Trp Val Ala Phe Tyr Asn Arg
    210                 215                 220

GTC ATG GGC TTC GTG AAC ATG GCC GAG TTC GTC GGT GAC GAC ATC GCC      720
Val Met Gly Phe Val Asn Met Ala Glu Phe Val Gly Asp Asp Ile Ala
225                 230                 235                 240

ACC GAG TAC TCG GCG CTG ATG AGC AAG GTC GTC GCC AAC GGC AAC CAC      768
Thr Glu Tyr Ser Ala Leu Met Ser Lys Val Val Ala Asn Gly Asn His
            245                 250                 255

CGG GTG AAG TTC CCG CTC AAC GAG CCG GCG GTC GGC AAG AGG AAG TCG      816
Arg Val Lys Phe Pro Leu Asn Glu Pro Ala Val Gly Lys Arg Lys Ser
        260                 265                 270

CAG ATC GAC GAG TAC CTG GAG TTC TAC CGC GGC GCC GGC TGC CAG CAC      864
Gln Ile Asp Glu Tyr Leu Glu Phe Tyr Arg Gly Ala Gly Cys Gln His
    275                 280                 285

ATC GCG CTG GCC ACC GGC GAC ATC CTG ACC ACC ATC AAG GCG ATG CGC      912
Ile Ala Leu Ala Thr Gly Asp Ile Leu Thr Thr Ile Lys Ala Met Arg
290                 295                 300

GAG GCC GGG GTG GAG TTC CTG GCC ACG CCC GAC TCC TAC TAC GAC GAC      960
Glu Ala Gly Val Glu Phe Leu Ala Thr Pro Asp Ser Tyr Tyr Asp Asp
305                 310                 315                 320

CCC GAG CTG CGG GCC CGC ATC GGC GAG GTG CGG CTG CCG ATC GAG ACG     1008
Pro Glu Leu Arg Ala Arg Ile Gly Glu Val Arg Leu Pro Ile Glu Thr
            325                 330                 335

CTC AAG GAG CAC GGC ATC CTC GTC GAC CGC GAC GAG GAC GGC TAC CTG     1056
Leu Lys Glu His Gly Ile Leu Val Asp Arg Asp Glu Asp Gly Tyr Leu
        340                 345                 350

CTG CAG ATC TTC ACC AAG CCG ATC GGC GAC CGG CCG ACC GTC TTC TAC     1104
Leu Gln Ile Phe Thr Lys Pro Ile Gly Asp Arg Pro Thr Val Phe Tyr
    355                 360                 365

GAG CTG ATC GAG CGG CAC GGT TCG CTG GGC TTC GGC AAG GGC AAC TTC     1152
Glu Leu Ile Glu Arg His Gly Ser Leu Gly Phe Gly Lys Gly Asn Phe
370                 375                 380

AAG GCG CTG TTC GAG GCG ATC GAG CGC GAG CAG GAG CGC CGC GGC AAC     1200
Lys Ala Leu Phe Glu Ala Ile Glu Arg Glu Gln Glu Arg Arg Gly Asn
385                 390                 395                 400

CTC TGA                                                             1206
Leu (2) INFORMATION FOR SEQ ID NO:3:

(i) SEQUENCE CHARACTERISTICS:
        (A) LENGTH: 401 amino acids
        (B) TYPE: amino acid
        (D) TOPOLOGY: linear (ii) MOLECULE TYPE: protein (xi) SEQUENCE DESCRIPTION: SEQ ID NO:3:

Val Thr Gly Thr Ile Asp Gln Gly Gln Ser Gly Gln Ile Asp Asp Val
 1               5                  10                  15

Thr Phe Asp Gln Met Arg Gln Leu Val Gly Leu Val Asp His Asp Ala
                20                  25                  30

Ser Lys Asp Pro Phe Pro Val Arg Ala Met Asp Ala Val Val Phe Val
            35                  40                  45
```

-continued

```
Val Gly Asn Ala Thr Gln Ser Ala Leu Phe Tyr Gln Val Ala Phe Gly
         50                  55                  60

Met Glu Leu Val Ala Tyr Ser Gly Pro Glu His Gly Asn Arg Asp His
 65                  70                  75                  80

Lys Ala Tyr Val Leu Lys Ser Gly Ser Ala Arg Phe Val Leu Lys Gly
                 85                  90                  95

Ala Val Asp Pro Asp Ser Pro Leu Ala Asp His Arg Arg His Gly
                100                 105                 110

Asp Gly Val Val Asp Leu Ala Leu Glu Val Thr Asp Val Asp Lys Cys
                115                 120                 125

Val Glu His Ala Arg Ala Gln Gly Ala Thr Val Leu Glu Glu Pro His
        130                 135                 140

Glu Val Ser Asp Asp Asn Gly Thr Val Arg Thr Ala Ala Ile Ala Thr
145                 150                 155                 160

Tyr Gly Glu Thr Arg His Thr Leu Val Asp Arg Ser Arg Tyr Arg Gly
                165                 170                 175

Pro Tyr Leu Pro Gly Tyr Val Glu Arg Thr Gly Ser Tyr Arg Lys Pro
                180                 185                 190

Glu Gly Ala Pro Lys Arg Leu Phe Gln Ala Val Asp His Cys Val Gly
        195                 200                 205

Asn Val Glu Leu Gly Lys Met Asp Glu Trp Val Ala Phe Tyr Asn Arg
210                 215                 220

Val Met Gly Phe Val Asn Met Ala Glu Phe Val Gly Asp Asp Ile Ala
225                 230                 235                 240

Thr Glu Tyr Ser Ala Leu Met Ser Lys Val Val Ala Asn Gly Asn His
                245                 250                 255

Arg Val Lys Phe Pro Leu Asn Glu Pro Ala Val Gly Lys Arg Lys Ser
                260                 265                 270

Gln Ile Asp Glu Tyr Leu Glu Phe Tyr Arg Gly Ala Gly Cys Gln His
        275                 280                 285

Ile Ala Leu Ala Thr Gly Asp Ile Leu Thr Thr Ile Lys Ala Met Arg
290                 295                 300

Glu Ala Gly Val Glu Phe Leu Ala Thr Pro Asp Ser Tyr Tyr Asp Asp
305                 310                 315                 320

Pro Glu Leu Arg Ala Arg Ile Gly Glu Val Arg Leu Pro Ile Glu Thr
                325                 330                 335

Leu Lys Glu His Gly Ile Leu Val Asp Arg Asp Glu Asp Gly Tyr Leu
                340                 345                 350

Leu Gln Ile Phe Thr Lys Pro Ile Gly Asp Arg Pro Thr Val Phe Tyr
        355                 360                 365

Glu Leu Ile Glu Arg His Gly Ser Leu Gly Phe Gly Lys Gly Asn Phe
370                 375                 380

Lys Ala Leu Phe Glu Ala Ile Glu Arg Glu Gln Glu Arg Arg Gly Asn
385                 390                 395                 400

Leu
```

(2) INFORMATION FOR SEQ ID NO:4:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Arg Asp Met Arg Ala Gln Val Thr Gly Arg Ala Val Gly Leu Arg
1               5                   10                  15

Arg Ser Cys Glu Leu Val Gly Leu Arg Pro Glu Asp Ser Leu Leu Leu
            20                  25                  30

Leu Leu Arg Ala Asp Leu Ala Asp Leu Ala Glu Asp Ala Gly Thr Asp
        35                  40                  45

Asn Pro Ala Val
    50

(2) INFORMATION FOR SEQ ID NO:5:

(i) SEQUENCE CHARACTERISTICS:
        (A) LENGTH: 241 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Arg Arg Ala Val Val Phe Gly Ala Ala Glu Leu Glu Ser Phe Val
1               5                   10                  15

Gln Glu Arg His Glu Pro Gly Arg Thr Glu Leu Ser Ile Glu Val Asp
            20                  25                  30

Val Glu Gly Leu Ala Leu Ala Gly Ala Ile Arg Ser His Glu Ile Asp
        35                  40                  45

Ile Val Asn Ala Ser Leu Ala Gly Leu Arg Ala Leu Leu Gly Ala Leu
    50                  55                      60

Ser Gly Pro Arg Asp Pro Leu Arg Val Arg Leu Ser Leu Tyr Arg Gly
65                  70                  75                  80

Ala Ser Thr Met Gly His Gln Ile Leu Gln Leu Met Leu Leu Pro Asp
            85                  90                  95

Ile Asn Gly Gly Ser Leu Val Val Ala Thr Pro Ser Gly Phe Gln Glu
        100                 105                 110

Pro His Glu Leu Leu Gly Ala Val Ala Ala Val Gly Ala Pro Glu Val
        115                 120                 125

Val Leu Lys Ala Arg Glu Leu Cys Leu Leu Leu Ala Arg Ser Leu Ala
130                 135                     140

Glu Glu Gly Val Thr Leu Val Asp Asp Val Leu Glu Ser Val His Ala
145                 150                 155                 160

Phe Thr Leu Glu Ser Pro Ala Pro Val Ala Ile Gly Asp Ala Met Thr
            165                 170                 175

Arg Gln Thr Asp Leu Leu Ala Val Pro Lys Gly Ala Ala Leu Ser Pro
        180                 185                 190

Pro Trp Ala Ala Ala Gln Glu Ala Gln Val Ala Leu Val Arg Val Gln
        195                 200                 205

Pro His Glu Ala Lys Val Ala Ala Ala Ile Gly Ser Val Leu Gly Gly
    210                 215                     220

Gly Gly Ala Pro Val Val Val Thr Arg Val Asp Pro Leu Gln Glu Leu
225                 230                 235                 240

Ile (2) INFORMATION FOR SEQ ID NO:6:

(i) SEQUENCE CHARACTERISTICS:
       (A) LENGTH: 380 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:6:

```
Met Thr Gln Thr Thr His His Thr Pro Asp Thr Ala Arg Gln Ala Asp
1               5                  10                  15

Pro Phe Pro Val Lys Gly Met Asp Ala Val Phe Ala Val Gly Asn
            20                  25                  30

Ala Lys Gln Ala Ala His Tyr Ser Thr Ala Phe Gly Met Gln Leu Val
        35                  40                  45

Ala Tyr Ser Gly Pro Glu Asn Gly Ser Arg Glu Thr Ala Ser Tyr Val
    50                  55                  60

Leu Thr Asn Gly Ser Ala Arg Phe Val Leu Thr Ser Val Ile Lys Pro
65                  70                  75                  80

Ala Thr Pro Trp Gly His Phe Leu Ala Asp His Val Ala Glu His Gly
            85                  90                  95

Asp Gly Val Val Asp Leu Ala Ile Glu Val Pro Asp Ala Arg Ala Ala
            100                 105                 110

His Ala Tyr Ala Ile Glu His Gly Ala Arg Ser Val Ala Glu Pro Tyr
        115                 120                 125

Glu Leu Lys Asp Glu His Gly Thr Val Val Leu Ala Ala Ile Ala Thr
    130                 135                 140

Tyr Gly Lys Thr Arg His Thr Leu Val Asp Arg Thr Gly Tyr Asp Gly
145                 150                 155                 160

Pro Tyr Leu Pro Gly Tyr Val Ala Ala Pro Ile Val Glu Pro Pro
            165                 170                 175

Ala His Arg Thr Phe Gln Ala Ile Asp His Cys Val Gly Asn Val Glu
        180                 185                 190

Leu Gly Arg Met Asn Glu Trp Val Gly Phe Tyr Asn Lys Val Met Gly
    195                 200                 205

Phe Thr Asn Met Lys Glu Phe Val Gly Asp Asp Ile Ala Thr Glu Tyr
    210                 215                 220

Ser Ala Leu Met Ser Lys Val Val Ala Asp Gly Thr Leu Lys Val Lys
225                 230                 235                 240

Phe Pro Ile Asn Glu Pro Ala Leu Ala Lys Lys Ser Gln Ile Asp
            245                 250                 255

Glu Tyr Leu Glu Phe Tyr Gly Gly Ala Gly Val Gln His Ile Ala Leu
            260                 265                 270

Asn Thr Gly Asp Ile Val Glu Thr Val Arg Thr Met Arg Ala Ala Gly
    275                 280                 285

Val Gln Phe Leu Asp Thr Pro Asp Ser Tyr Tyr Asp Thr Leu Gly Glu
    290                 295                 300

Trp Val Gly Asp Thr Arg Val Pro Val Asp Thr Leu Arg Glu Leu Lys
305                 310                 315                 320

Ile Leu Ala Asp Arg Asp Glu Asp Gly Tyr Leu Leu Gln Ile Phe Thr
                325                 330                 335

Lys Pro Val Gln Asp Arg Pro Thr Val Phe Phe Glu Ile Ile Glu Arg
            340                 345                 350
```

```
His Gly Ser Met Gly Phe Gly Lys Gly Asn Phe Lys Ala Leu Phe Glu
            355                 360                 365

Ala Ile Glu Arg Glu Gln Glu Lys Arg Gly Asn Leu
        370                 375                 380

(2) INFORMATION FOR SEQ ID NO:7:

(i) SEQUENCE CHARACTERISTICS:
        (A) LENGTH: 358 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Met Ala Asp Leu Tyr Glu Asn Pro Met Gly Leu Met Gly Phe Glu Phe
1                   5                   10                  15

Ile Glu Leu Ala Ser Pro Thr Pro Asn Thr Leu Glu Pro Ile Phe Glu
                20                  25                  30

Ile Met Gly Phe Thr Lys Val Ala Thr His Arg Ser Lys Asp Val His
            35                  40                  45

Leu Tyr Arg Gln Gly Ala Ile Asn Leu Ile Leu Asn Asn Glu Pro His
        50                  55                  60

Ser Val Ala Ser Tyr Phe Ala Ala Glu His Gly Pro Ser Val Cys Gly
65                  70                  75                  80

Met Ala Phe Arg Val Lys Asp Ser Gln Lys Ala Tyr Lys Arg Ala Leu
                85                  90                  95

Glu Leu Gly Ala Gln Pro Ile His Ile Glu Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Phe
130                 135                 140

Leu Glu Gly Val Asp Arg His Pro Val Gly Ala Gly Leu Lys Ile Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ile Arg Tyr Phe Asp
            180                 185                 190

Ile Lys Gly Glu Tyr Thr Gly Leu Thr Ser Lys Ala Met Thr Ala Pro
        195                 200                 205

Asp Gly Met Ile Arg Ile Pro Leu Asn Glu Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Ser Asp Asp Leu Ile Lys Thr Trp Asp His Leu
                245                 250                 255

Lys Ser Ile Gly Met Arg Phe Met Thr Ala Pro Pro Asp Thr Tyr Tyr
            260                 265                 270

Glu Met Leu Glu Gly Arg Leu Pro Asn His Gly Glu Pro Val Gly Glu
        275                 280                 285

Leu Gln Ala Arg Gly Ile Leu Leu Asp Gly Ser Ser Glu Ser Gly Asp
        290                 295                 300

Lys Arg Leu Leu Leu Gln Ile Phe Ser Glu Thr Leu Met Gly Pro Val
305                 310                 315                 320
```

```
Phe Phe Glu Phe Ile Gln Arg Lys Gly Asp Asp Gly Phe Gly Glu Gly
            325                 330                 335

Asn Phe Lys Ala Leu Phe Glu Ser Ile Glu Arg Asp Gln Val Arg Arg
            340                 345                 350

Gly Val Leu Ser Thr Asp
        355

(2) INFORMATION FOR SEQ ID NO:8:

(i) SEQUENCE CHARACTERISTICS:
        (A) LENGTH: 404 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Met Ser Glu Asn Lys Asp His Val Val Gly Tyr Thr Glu Lys Pro
1               5                   10                  15

Val Gly Glu Arg Pro Thr Gly Gly Lys Phe Leu Gly Tyr Asp His Leu
            20                  25                  30

His Phe Trp Val Gly Asn Ala Lys Gln Ala Ala Gly Trp Tyr Thr Ser
            35                  40                  45

Arg Phe Gly Phe Glu Tyr Tyr Ala Tyr Lys Gly Leu Glu Thr Gly Ser
        50                  55                  60

Arg Glu Val Ala Thr His Val Val Arg Asn Lys Gln Gly Val Thr Leu
65                  70                  75                  80

Ala Phe Ser Thr Pro Tyr Gly Asn Asp Lys Asp Asn Gln Arg Glu Met
            85                  90                  95

Asn Gln His Gln Ser Leu His Gly Asp Gly Val Lys Asp Val Ala Phe
            100                 105                 110

Ala Val Glu Asp Cys His Ser Ile Tyr Asn Lys Ala Ile Gln Arg Gly
            115                 120                 125

Ala Lys Cys Ala Tyr Pro Pro Gln Asp Leu Lys Asp Glu His Gly Ser
        130                 135                 140

Val Thr Ile Ala Ala Val His Thr Tyr Gly Glu Val Ile His Thr Phe
145                 150                 155                 160

Ile Gln Arg Asn Asp Tyr Lys Gly Phe Phe Met Pro Gly Phe Val Ala
            165                 170                 175

His Pro Leu Lys Asp Pro Leu Asn Asn Val Leu Pro Asp Ile Ser Tyr
            180                 185                 190

Asn Tyr Val Asp His Ile Val Gly Asn Gln Pro Asp Asn Met Met Thr
        195                 200                 205

Ser Ala Ala Asp Trp Tyr Glu Lys Thr Leu Asp Phe His Arg Phe Trp
210                 215                 220

Ser Val Asp Asp Ser Met Ile His Thr Glu Phe Ser Ser Leu Arg Ser
225                 230                 235                 240

Ile Val Met Thr Asp Tyr Asp Gln Lys Ile Lys Met Pro Ile Asn Glu
            245                 250                 255

Pro Ala Asp Gly Lys Arg Lys Ser Gln Ile Gln Glu Tyr Ile Asp Phe
            260                 265                 270

Tyr Ala Gly Pro Gly Val Gln His Ile Ala Leu Asn Thr Ser Asp Val
        275                 280                 285

Ile Asn Thr Val Glu Gly Leu Arg Ala Arg Gly Val Glu Phe Leu Ser
        290                 295                 300
```

```
Ile Pro Thr Ser Tyr Tyr Asp Asn Leu Arg Lys Ala Leu Thr Ala Gln
305                 310                 315                 320

Thr Ser Ile Thr Val Lys Glu Asp Leu Asp Val Leu Gln Lys Asn His
            325                 330                 335

Ile Leu Val Asp Tyr Asp Glu Lys Gly Tyr Leu Leu Gln Ile Phe Thr
                340                 345                 350

Lys Pro Val Glu Asp Arg Pro Thr Leu Phe Tyr Glu Ile Ile Gln Arg
            355                 360                 365

Asn Asn His Gln Gly Phe Gly Ala Gly Asn Phe Lys Ser Leu Phe Val
        370                 375                 380

Ser Leu Glu Leu Glu Gln Glu Lys Arg Gly Asn Leu Thr Glu Ile Val
385                 390                 395                 400

Lys Asn Ile Tyr
```

(2) INFORMATION FOR SEQ ID NO:9:

(i) SEQUENCE CHARACTERISTICS:
        (A) LENGTH: 399 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met Ala Pro Ala Ala Asp Ser Pro Thr Leu Gln Pro Ala Gln Pro Ser
1               5                   10                  15

Asp Leu Asn Gln Tyr Arg Gly Tyr Asp His Val His Trp Tyr Val Gly
                20                  25                  30

Asn Ala Lys Gln Ala Ala Thr Tyr Tyr Val Thr Arg Met Gly Phe Glu
            35                  40                  45

Arg Val Ala Tyr Arg Gly Leu Glu Thr Gly Ser Lys Ala Val Ala Ser
        50                  55                  60

His Val Val Arg Asn Gly Asn Ile Thr Phe Ile Leu Thr Ser Pro Leu
65                  70                  75                  80

Arg Ser Val Glu Gln Ala Ser Arg Phe Pro Glu Asp Glu Ala Leu Leu
                85                  90                  95

Lys Glu Ile His Ala His Leu Glu Arg His Gly Asp Gly Val Lys Asp
            100                 105                 110

Val Ala Phe Glu Val Asp Cys Val Glu Ser Val Phe Ser Ala Ala Val
        115                 120                 125

Arg Asn Gly Ala Glu Val Val Ser Asp Val Arg Thr Val Glu Asp Glu
130                 135                 140

Asp Gly Gln Ile Lys Met Ala Thr Ile Arg Thr Tyr Gly Glu Thr Thr
145                 150                 155                 160

His Thr Leu Ile Glu Arg Ser Gly Tyr Arg Gly Phe Met Pro Gly
                165                 170                 175

Tyr Arg Met Glu Ser Asn Ala Asp Ala Thr Ser Lys Phe Leu Pro Lys
                180                 185                 190

Val Val Leu Glu Arg Ile Asp His Cys Val Gly Asn Gln Asp Trp Asp
        195                 200                 205

Glu Met Glu Arg Val Cys Asp Tyr Tyr Glu Lys Ile Leu Gly Phe His
    210                 215                 220

Arg Phe Trp Ser Val Asp Asp Lys Asp Ile Cys Thr Glu Phe Ser Ala
225                 230                 235                 240
```

```
Leu Lys Ser Ile Val Met Ala Ser Pro Asn Asp Ile Val Lys Met Pro
                245                 250                 255

Ile Asn Glu Pro Ala Lys Gly Lys Lys Gln Ser Gln Ile Glu Glu Tyr
            260                 265                 270

Val Asp Phe Tyr Asn Gly Ala Gly Val Gln His Ile Ala Leu Arg Thr
            275                 280                 285

Asn Asn Ile Ile Asp Ala Ile Thr Asn Leu Lys Ala Arg Gly Thr Glu
        290                 295                 300

Phe Ile Lys Val Pro Glu Thr Tyr Tyr Glu Asp Met Lys Ile Arg Leu
305                 310                 315                 320

Lys Arg Gln Gly Leu Val Leu Asp Glu Asp Phe Glu Thr Leu Lys Ser
                325                 330                 335

Leu Asp Ile Leu Ile Asp Phe Asp Glu Asn Gly Tyr Leu Leu Gln Leu
                340                 345                 350

Phe Thr Lys His Leu Met Asp Arg Pro Thr Val Phe Ile Glu Ile Ile
            355                 360                 365

Gln Arg Asn Asn Phe Ser Gly Phe Gly Ala Gly Asn Phe Arg Ala Leu
        370                 375                 380

Phe Glu Ala Ile Glu Arg Glu Gln Ala Leu Arg Gly Thr Leu Ile
385                 390                 395
```

(2) INFORMATION FOR SEQ ID NO:10:

(i) SEQUENCE CHARACTERISTICS:
        (A) LENGTH: 346 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Ala Ser Glu Gln Asn Pro Leu Gly Leu Leu Gly Ile Glu Phe Thr
1               5                   10                  15

Glu Phe Ala Thr Pro Asp Leu Asp Phe Met His Lys Val Phe Ile Asp
            20                  25                  30

Phe Gly Phe Ser Lys Leu Lys Lys His Lys Gln Lys Asp Ile Val Tyr
        35                  40                  45

Tyr Lys Gln Asn Asp Ile Asn Phe Leu Leu Asn Asn Glu Lys Gln Gly
    50                  55                  60

Phe Ser Ala Gln Phe Ala Lys Thr His Gly Pro Ala Ile Ser Ser Met
65                  70                  75                  80

Gly Trp Arg Val Glu Asp Ala Asn Phe Ala Phe Glu Gly Ala Val Ala
                85                  90                  95

Arg Gly Ala Lys Pro Ala Ala Asp Glu Val Lys Asp Leu Pro Tyr Pro
            100                 105                 110

Ala Ile Tyr Gly Ile Gly Asp Ser Leu Ile Tyr Phe Ile Asp Thr Phe
        115                 120                 125

Gly Asp Asp Asn Asn Ile Tyr Thr Ser Asp Phe Glu Ala Leu Asp Glu
    130                 135                 140

Pro Ile Ile Thr Gln Glu Lys Gly Phe Ile Glu Val Asp His Leu Thr
145                 150                 155                 160

Asn Asn Val His Lys Gly Thr Met Glu Tyr Trp Ser Asn Phe Tyr Lys
                165                 170                 175

Asp Ile Phe Gly Phe Thr Glu Val Arg Tyr Phe Asp Ile Lys Gly Ser
            180                 185                 190
```

```
Gln Thr Ala Leu Ile Ser Tyr Ala Leu Arg Ser Pro Asp Gly Ser Phe
            195                 200                 205

Cys Ile Pro Ile Asn Glu Gly Lys Gly Asp Asp Arg Asn Gln Ile Asp
210                 215                 220

Glu Tyr Leu Lys Glu Tyr Asp Gly Pro Gly Val Gln His Leu Ala Phe
225                 230                 235                 240

Arg Ser Arg Asp Ile Val Ala Ser Leu Asp Ala Met Glu Gly Ser Ser
            245                 250                 255

Ile Gln Thr Leu Asp Ile Ile Pro Glu Tyr Tyr Asp Thr Ile Phe Glu
            260                 265                 270

Lys Leu Pro Gln Val Thr Glu Asp Arg Asp Arg Ile Lys His His Gln
            275                 280                 285

Ile Leu Val Asp Gly Asp Glu Asp Gly Tyr Leu Leu Gln Ile Phe Thr
            290                 295                 300

Lys Asn Leu Phe Gly Pro Ile Phe Ile Glu Ile Ile Gln Arg Lys Asn
305                 310                 315                 320

Asn Leu Gly Phe Gly Glu Gly Asn Phe Lys Ala Leu Phe Glu Ser Ile
            325                 330                 335

Glu Arg Asp Gln Val Arg Arg Gly Val Leu
            340                 345

(2) INFORMATION FOR SEQ ID NO:11:

(i) SEQUENCE CHARACTERISTICS:
        (A) LENGTH: 393 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Met Thr Thr Tyr Ser Asp Lys Gly Ala Lys Pro Glu Arg Gly Arg Phe
1               5                   10                  15

Leu His Phe His Ser Val Thr Phe Trp Val Gly Asn Ala Lys Gln Ala
            20                  25                  30

Ala Ser Phe Tyr Cys Ser Lys Met Gly Phe Glu Pro Leu Ala Tyr Arg
            35                  40                  45

Gly Leu Glu Thr Gly Ser Arg Glu Val Val Ser His Val Ile Lys Gln
50                  55                  60

Gly Lys Ile Val Phe Val Leu Ser Ser Ala Leu Asn Pro Trp Asn Lys
65                  70                  75                  80

Glu Met Gly Asp His Leu Val Lys His Gly Asp Gly Val Lys Asp Ile
            85                  90                  95

Ala Phe Glu Val Glu Asp Cys Asp Tyr Ile Val Gln Lys Ala Arg Glu
            100                 105                 110

Arg Gly Ala Lys Ile Met Arg Glu Pro Trp Val Glu Gln Asp Lys Phe
            115                 120                 125

Gly Lys Val Lys Phe Ala Val Leu Gln Thr Tyr Gly Asp Thr Thr His
            130                 135                 140

Thr Leu Val Glu Lys Met Asn Tyr Ile Gly Gln Phe Leu Pro Gly Tyr
145                 150                 155                 160

Glu Ala Pro Ala Phe Met Asp Pro Leu Leu Pro Lys Leu Pro Lys Cys
            165                 170                 175

Ser Leu Glu Met Ile Asp His Ile Val Gly Asn Gln Pro Asp Gln Glu
            180                 185                 190
```

-continued

```
Met Val Ser Ala Ser Glu Trp Tyr Leu Lys Asn Leu Gln Phe His Arg
        195                 200                 205

Phe Trp Ser Val Asp Asp Thr Gln Val His Thr Glu Tyr Ser Ser Leu
        210                 215                 220

Arg Ser Ile Val Val Ala Asn Tyr Glu Glu Ser Ile Lys Met Pro Ile
225                 230                 235                 240

Asn Glu Pro Ala Pro Gly Lys Lys Lys Ser Gln Ile Gln Glu Tyr Val
                245                 250                 255

Asp Tyr Asn Gly Gly Ala Gly Val Gln His Ile Ala Leu Lys Thr Glu
                260                 265                 270

Asp Ile Ile Thr Ala Ile Arg His Leu Arg Glu Arg Gly Leu Glu Phe
        275                 280                 285

Leu Ser Val Pro Ser Thr Tyr Tyr Lys Gln Leu Arg Glu Lys Leu Lys
        290                 295                 300

Thr Ala Lys Ile Lys Val Lys Glu Asn Ile Asp Ala Leu Glu Glu Leu
305                 310                 315                 320

Lys Ile Leu Val Asp Tyr Asp Glu Lys Gly Tyr Leu Leu Gln Ile Phe
                325                 330                 335

Thr Lys Pro Val Gln Asp Arg Pro Thr Leu Phe Leu Glu Val Ile Gln
                340                 345                 350

Arg His Asn His Gln Gly Phe Gly Ala Gly Asn Phe Asn Ser Leu Phe
                355                 360                 365

Lys Ala Phe Glu Glu Gln Asn Leu Arg Gly Asn Leu Thr Asn Met
        370                 375                 380

Glu Thr Asn Gly Val Val Pro Gly Met
385                 390
```

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GTAAGCTTCG ACCAGATGCG CCAG     24

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TGGAATTCCC TCTTGCCGAC CGCC     24